US007087395B1

(12) United States Patent
Garrity et al.

(10) Patent No.: US 7,087,395 B1
(45) Date of Patent: Aug. 8, 2006

(54) VITAMIN D ASSAY

(75) Inventors: Martha Garrity, San Clemente, CA (US); Jacqueline Tran, Westminster, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 85 days.

(21) Appl. No.: 09/761,969

(22) Filed: Jan. 16, 2001

(51) Int. Cl.
- *G01N 33/53* (2006.01)
- *G01N 33/543* (2006.01)
- *G01N 21/00* (2006.01)

(52) U.S. Cl. .................. 435/7.93; 435/7.1; 435/7.9; 435/7.92; 436/501; 436/518; 436/536; 436/542; 422/61; 424/1.49; 536/23.1; 536/24.3; 536/24.33

(58) Field of Classification Search .............. 436/501, 436/536, 542, 518; 424/1.49; 435/6, 7.1–7.9, 435/91.2, 7.92, 7.93; 536/23.1, 24.3, 24.33; 422/6, 1
See application file for complete search history.

(56) References Cited

U.S. PATENT DOCUMENTS

| | | | |
|---|---|---|---|
| 3,654,090 A | 4/1972 | Schuurs et al. ........... 195/103.5 |
| 3,791,932 A | 2/1974 | Schuurs et al. ........ 195/103.5 R |
| 3,817,837 A | 6/1974 | Rubenstein et al. .. 195/103.5 R |
| 3,839,153 A | 10/1974 | Shuurs et al. ............ 195/103 R |
| 3,850,578 A | 11/1974 | McConnell ................ 23/230 B |
| 3,850,752 A | 11/1974 | Schuurs et al. ............. 195/103 |
| 3,879,262 A | 4/1975 | Schuurs et al. ................ 195/63 |
| 3,880,934 A | 4/1975 | Rammler ................ 260/613 D |
| 3,901,654 A | 8/1975 | Gross ........................ 23/230 B |
| 4,121,975 A * | 10/1978 | Ullman et al. ................ 435/7.9 |
| 4,380,580 A | 4/1983 | Boguslaski et al. ............. 435/7 |
| 4,444,879 A * | 4/1984 | Foster et al. ................ 435/7.95 |
| 4,816,417 A | 3/1989 | DeLuca et al. .............. 436/501 |
| 4,935,339 A | 6/1990 | Zahradnik ....................... 435/5 |
| 4,956,303 A | 9/1990 | Self ........................... 436/542 |
| 5,064,770 A * | 11/1991 | DeLuca et al. ............. 436/542 |
| 5,110,833 A | 5/1992 | Mosbach ....................... 521/50 |
| 5,110,932 A | 5/1992 | Law et al. ................... 546/102 |
| 5,202,266 A | 4/1993 | Nakagawa et al. .......... 436/501 |
| 5,232,836 A | 8/1993 | Bouillon et al. ................. 435/8 |
| 5,281,712 A | 1/1994 | McCapra et al. ............ 546/104 |
| 5,283,334 A | 2/1994 | McCapra .................... 546/104 |
| 5,284,951 A | 2/1994 | McCapra et al. ........... 546/107 |
| 5,284,952 A | 2/1994 | Ramakrishnan ............. 546/104 |
| 5,290,936 A | 3/1994 | Beheshti et al. ............. 546/104 |
| 5,321,136 A | 6/1994 | McCapra .................... 546/104 |
| 5,338,847 A | 8/1994 | McCapra .................... 546/104 |
| 5,395,938 A | 3/1995 | Ramakrishnan ............. 546/104 |
| 5,538,901 A | 7/1996 | Law et al. ................... 436/501 |
| 5,641,690 A | 6/1997 | Self ........................... 436/548 |
| 5,705,622 A | 1/1998 | McCapra .................... 536/23.1 |
| 5,770,176 A * | 6/1998 | Nargessi ..................... 424/1.49 |
| 5,807,675 A | 9/1998 | Davalian et al. ................ 435/6 |
| 5,821,020 A | 10/1998 | Hollis ........................... 436/63 |
| 5,840,867 A | 11/1998 | Toole et al. ................ 536/23.1 |
| 5,981,779 A | 11/1999 | Holick et al. ................ 552/653 |

FOREIGN PATENT DOCUMENTS

| | | |
|---|---|---|
| DE | 198 40 435 | 12/1999 |
| EP | 0 750 743 | 1/1997 |
| GB | 1392403 | 4/1975 |
| WO | WO89/05356 | * 6/1989 |

OTHER PUBLICATIONS

Kobayashi et al., "Evaluation of solubilizing agents for 25-hydroxy-vitamin D3 immunoassay." Clinica Chimica Acta, 1992, pp. 83-88.*

Aldrich Catalogue, 1992, pp. 1949-1950.*

"Measurement of Calcium, Phosphate, Parathyroid Hormone, and Vitamin D" by Heinrich Schmidt-Gayk; *Dynamics of Bone and Cartilage Metabolism* pp. 375-399; (1999).

"Determination of vitamin D3 metabolites: state-of-the-art and trends" by Luque de Castro et al.; *Journal of Pharmaceutical and Biomedical Analysis* 20 (1999) pp. 1-17.

"Two Direct (Nonchromatographic) Assays for 25-Hydroxyvitamin D" by Bouillon et al.; *Clinical Chemistry*, vol. 30 No. 11 pp 1731-1736; (1984).

Directional insert of Biosource International Europe S.A. entitled: "OH-VIT.D3-RIA-CT".

Directional insert of IDS, Inc. entitled: "Gamma-B 25-Hydroxy Vitamin D RIA" AA-35PS, Jan. 6, 1999, issue 3.

Directional insert of Nichols Institute Diagnostics entitled: "25-OH-D 60T kit".

Instruction Manual of Incstar Corporation (Jul. 1992).

Instruction manual for Jummn Diagnostik entitled: "25OHVitamin D Enzume-based-Protein-Binding-Assay".

Competitive protien-Binding Radioassays for 25-OH-D; Clinical Applications; by Hadda, Jr.

"The Simultaneous Measurement of Vitamin D Metabolites in Plasma: Studies in Healthy Adults and in Patients with Calcium Nephrolithiasis" by Caldas, A.E., et al.; *Journal of Laboratory and Clinical Medicine*, St. Louis, MO, vol. 91, No. 5, (1978) pp. 840-849.

"A Direct Non-Extraction Enzyme Immunoassay for Measurement of 25 Hydroxyvitamin D" by Gardner, M.J., et al.; *Journal of Bone and Mineral Research*, New York, NY., vol. 16, No. Suppl 1, Sep. 2001 p. S434, ANSU528.

(Continued)

*Primary Examiner*—Long V. Le
*Assistant Examiner*—Lisa V. Cook
(74) *Attorney, Agent, or Firm*—Stout, Uxa, Buyan & Mullins, LLP; Donald E. Stout; Greg S. Hollrigel

(57) ABSTRACT

The present invention features a kit and a method of using the kit for determining a concentration of a vitamin D component. The kit comprises a releasing composition and a detecting composition. The releasing composition comprises an aqueous base component. In one embodiment, the releasing composition is substantially free from an organic solvent.

17 Claims, 2 Drawing Sheets

OTHER PUBLICATIONS

"Comparison of the Nichols Advantage and the Conventional Competitive Protein Binding Assay for the Measurement of Circulating Concentration of 25-Hydroxyvitamin D in Human and Non-Human Primates." by Chen, T.C., et al.; *Journal of Bone and Mineral Research,* vol. 16, No. Suppl 1; Sep. 2001, p. S434.

PCT International Search Report; Jun. 6, 2003.

* cited by examiner

 A vitamin D component added to the assay system to compete with the released vitamin D component.

 A vitamin D component released by the releasing composition.

 A vitamin D binding protein, for example DBP.

 A solid phase, for example, a magnetic particle.

 A host component, for example an antibody, which recognizes a vitamin D component.

 A molecule which can bind to a biotin, for example streptavidin or avidin.

 A label, for example acridinium.

 A biotin.

 A protein, for example an antibody, capable of binding to a vitamin D component at a site other than the one that is recognized by a host component.

 Means that one entity is linked to another entity. The linkage may be direct, or through another molecule or molecules.

 Means that one entity is linked to another entity. The linkage may be direct, or through another molecule or molecules.

FIG. 1B

VITAMIN D ASSAY

BACKGROUND OF THE INVENTION

In 1928 Adolf Windaus was awarded the Nobel Prize in chemistry for his research on substances of significant biological importance. One of these substances was Vitamin D. Since then, much more is known about vitamin D, its chemistry and its pharmacological effects and dynamics.

Vitamin D is not widely found in food, but rather, it is produced by the skin. Once produced, it undergoes 25-hydroxylation to form a 25-hydroxy-D (25-OH-D) in the liver. The circulating concentration of 25-OH-D is considered to be an important indicator of vitamin D status in man. For example, hypovitaminosis, which results from the insufficient endogenous production of vitamin D in the skin, and insufficient dietary supplementation, and/or inability of the small intestine to absorb adequate amounts of vitamin D from dietary sources, results in hypocalcemia and hypophosphatemia and corresponding secondary hyperparathyroidism. Hypovitaminosis D also results in disturbances in mineral metabolism (i.e., rickets and osteomalacia in children and adults, respectively).

Serum 25-OH-D-levels are also found to be lower than normal in intestinal malabsorption syndromes, liver disorders (chronic and acute), and nephrotic syndromes. In osteopenia, especially in the aged, serum 25-OH-D levels are often found to be lower than normal. In cases of vitamin D intoxication, serum 25-OH-D level is found, as expected, to be higher than normal.

Once hydroxylated, 25-OH-D is again hydroxylated in the kidney to give the hormonal form 1,25-dihydroxy-vitamin D (1,25-$(OH)_2$-D). The 1,25-$(OH)_2$-D level in blood is also an important indicator of certain diseases. For example, a low level of 1,25-$(OH)_2$-D is indicative of kidney failure and/or osteoporosis.

Considering their pathological importance, tremendous efforts have been directed towards developing assays for accurately measuring concentrations of 25-OH-D and/or 1,25-$(OH)_2$-D in circulation.

For example, 25-OH-D concentrations in blood have been measured by high performance liquid chromatography (HPLC) and by competitive protein binding assays (Eisman et al., Anal. Biochem. 80: 298–305 (1977); and Haddad et al., J. Clin. Endocr. 33: 992–995 (1971)). For example, the vitamin D transport protein known as DBP, which has a strong preference for binding 25-OH-D was used in the competitive binding assay (Bouillion et al., J. Steroid Biochem. 13: 1029–1034 (1980)).

Also, various competitive binding assays have been employed to assay for the presence of 1,25-$(OH)_2$-D. (Shigeharu et al., Anal. Biochem. 116: 211–222 (1981); Eisman et al., Arch. Biochem. Biophys. 176: 235–243 (1976); Perry et al., Biochem. Biophys. Res. Comm. 112: 431–436 (1983); Bouillion et al., Ann. Endocrin. 41: 435–436 (1980); Bouillion, Clin. Chem. 26: 562–567 (1980); Bouillion, Eur. J. Biochem. 66: 285–291 (1976)). In such assays, vitamin D and its metabolites were extracted from blood serum or plasma with an organic solvent. The extract was then purified by column chromatography and HPLC to yield 1,25-$(OH)_2$-D. The purified 1,25-$(OH)_2$-D was then measured.

In general, most assays presently being employed in the art to determine the concentration of vitamin D are heterogeneous assays. Furthermore, most of these assays rely on the addition of an organic solvent to release the vitamin D and/or vitamin D metabolites from the binding proteins, for example DBP. (Schmidt-Gayk, Dynamics of Bone and Cartilage Metabolism, Chapter 26, Table V). That is, the addition of organic solvent to the samples causes denaturation and precipitation of the serum proteins including DBP, and subsequently, the precipitated protein can be spun out of solution and the released metabolites remain in solution in the organic layer. This organic layer containing the released metabolite is then extracted and transferred into another system for analysis.

Although the present existing assay systems are useful, their reliance on an organic solvent to release the vitamin D and/or vitamin D metabolite is problematic. The problems with using an organic solvent include: (A) difficulties in the handling of volatile organic solvents, (B) laborious manual extractions, (C) loss of patient, identification since two transfer steps are required, and (D) loss of precision in measurement.

The loss in precision may be caused by the heterogeneous extraction step, since heterogeneous extraction can be very technique dependent. For example, in a heterogeneous extraction step, some matrix components may be extracted along with the organic layer containing the metabolite. One such matrix component is lipid, which has been shown to cause an elevated measurement of the metabolite values.

There is a need to have improved kits and methods for determining the concentration of vitamin D and its metabolites in a body fluid of a mammal.

SUMMARY OF THE INVENTION

In accordance with the present invention, a kit is featured for determining the concentration of a vitamin D component. In a broad embodiment, the kit comprises a releasing composition. The releasing composition facilitates in releasing the vitamin D component from a vitamin D component binding-protein. In one embodiment, the releasing composition is substantially free of an organic solvent. In one embodiment, the kit further comprises a detecting composition. The detecting composition facilitates in determining the concentration of the vitamin D component.

Further in accordance with the present invention, a kit according to this invention may be useful for determining the concentration of the vitamin D component present in a mammal fluid. The mammal fluid may be milk, whole blood, serum, plasma and mixtures thereof. For example, a mammal fluid may comprise a human serum.

Still further in accordance with the present invention, the vitamin D component may be a vitamin D, a precursor of a vitamin D, a metabolite of a vitamin D and mixtures thereof. For example, a vitamin D component comprises a 25-OH-D.

Still further in accordance with the present invention, the releasing composition comprises an aqueous base component, for example, NaOH or KOH. In one embodiment, the releasing composition comprises about 0.1 to about 1.0 M of the aqueous base component. In one embodiment, the releasing composition is substantially free of an organic solvent. In one embodiment, the releasing composition may be adapted to various bio-assay systems to assay for a vitamin D component.

Still further in accordance with the present invention, the releasing composition further comprises a cyclo-oligomer component, for example a cyclodextrin, derivatives thereof and mixtures thereof. In one embodiment, the releasing composition comprises about 0.01 to about 5% of the cyclo-oligomer component.

Still further in accordance with the present invention, the releasing component further comprises about 0.5 to about 5% of a metal salicylate, including sodium salicylate.

Still further in accordance with the present invention, the releasing component further comprises about 0.01 to about 0.1% of a surfactant.

Still further in accordance with the present invention, the releasing composition forms a homogeneous mixture with a mammal fluid.

Still further in accordance with the present invention, the detecting composition comprises a host component and a partner component, wherein the host component binds to the partner component to form a partner/host complex. The concentration of the complex should be proportional to the concentration of the vitamin D component. In one embodiment, the concentration of the complex is inversely proportional to is the concentration of the vitamin D component. In one embodiment, the host component comprises an antibody and/or portions thereof.

Still further in accordance with the present invention, the host component is labeled. In one embodiment, the host component is labeled with a chemiluminescent label, for example acridinium, a fluorescent label and/or a radio-active label.

Still further in accordance with the present invention, the partner component comprises a vitamin D component linked to a separator component, wherein the separator component is a solid phase, such as antibody or a magnetic particle.

Still further in accordance with the present invention, the partner component binds to the host component through at least one intermediate binding component, for example, a vitamin D binding-protein.

Still further in accordance with the present invention, a method is featured for assaying a body fluid sample for the concentration of a vitamin D component. The method comprises the steps of releasing the vitamin D component from the vitamin D component binding-protein by contacting the sample with a releasing composition in a holder, and determining the concentration of the vitamin D component.

Still further in accordance with the present invention, the determining step includes the steps of (a) adding a detecting composition to the holder, the detecting composition comprises a host component and a partner component, the host component binds to the partner component to form a partner/host complex, (b) isolate the complex in the tube, (c) measuring the concentration of the complex by measuring the concentration of the host component in the complex, the concentration of the complex is proportional to the concentration of the vitamin D component.

Any feature or combination of features described herein are included within the scope of the present invention provided that the features included in any such combination are not mutually inconsistent as will be apparent from the context, this specification, and the knowledge of one of ordinary skill in the art.

BRIEF DESCRIPTION OF THE DRAWINGS

FIG. 1B is a legend of the elements of FIG. 1A.

Figure 1A:
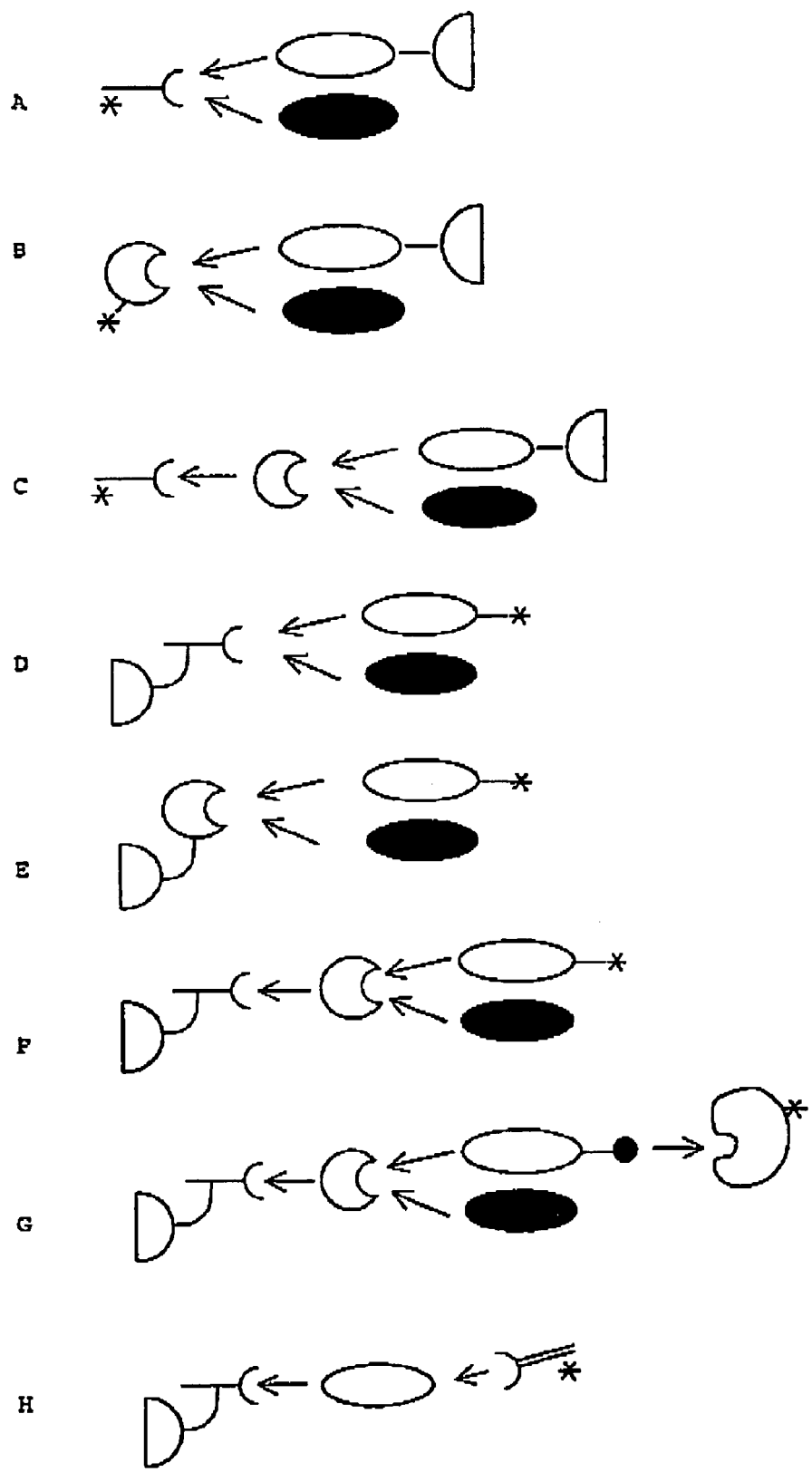
FIG. 1A is an illustration of general assays (A through H) in which a releasing composition may be employed.

Additional advantages and aspects of the present invention are apparent in the following detailed description and claims.

DETAILED DESCRIPTION OF THE INVENTION

In a broad embodiment, the present invention provides a kit for determining the concentration of a vitamin D component. In one embodiment, the kit is useful for determining the concentration of a vitamin D component found in a mammal, for example a human. In a preferred embodiment, the kit is useful for determining the concentration of a vitamin D component in a body fluid of a mammal. The body fluid may include, without limitation, milk, whole blood, serum, plasma or mixtures thereof. Preferably, the body fluid is serum of a human.

A vitamin D component includes a vitamin D, vitamin D precursors and vitamin metabolites. Without intending to be limited by the examples, a vitamin D component may include, for example, vitamin $D_2$, $D_3$, $D_4$, $D_5$, and $D_6$; precursors of a vitamin D such as 7-dehydrocholesterol; and metabolites of vitamin D such as metabolites of vitamin $D_2$, $D_3$, $D_4$, $D_5$, and $D_6$, preferably 1,25-OH-$D_2$, and more preferably 25-OH-D. Often, a vitamin D component is bound to a vitamin D component binding protein. For example, in human serum, 25-OH-D is bound to a protein; this protein is commonly referred to in the art as a DBP.

A kit of the present invention comprises a releasing composition. The releasing composition of this invention is adaptable for use in or with various bio-assay techniques known in the art to determine the concentration of a vitamin D component. Preferably, the releasing composition of the present invention substantially eliminates the need to purify the vitamin D component prior to determining its concentration. Also preferably, a bio-assay kit comprising a releasing composition of this invention has improved precision in the measurement of a vitamin D component.

In one embodiment, the releasing composition comprises an aqueous base component and facilitates in releasing the vitamin D component from a binding entity. The binding entity includes, without limitation, a binding protein or a binding lipid. The aqueous base component comprises any molecule which is effective in raising and maintaining the pH of the releasing composition to a pH of greater than 7, preferably greater than 8, more preferably about 12 to about 14, even more preferably about 13. In one embodiment, the base component comprises a metal hydroxide, for example a NaOH and/or a KOH. In one embodiment, the releasing composition is substantially free of an organic solvent, for example acetonitrile.

In a preferred embodiment, the releasing composition comprises about 0.1 to about 1 M of the aqueous base component. More preferably, the releasing composition comprises about 0.35 to about 0.5 M of the aqueous base component. For example, a releasing composition in accordance with the present invention may include about 0.35 to about 0.5 M of NaOH.

Without wishing to limit the invention to any particular theory or mechanism of operation, it is believed that the aqueous base component denatures, preferably irreversibly denatures, the vitamin D binding protein, i.e. DBP, and causes the bound vitamin D component to be released. Additionally, the aqueous base component may also irreversibly denature other plasma or serum proteins, such as albumin. It is further believed that these proteins may interfere in the detection of the vitamin D component and their denaturation reduces this effect.

In one embodiment, the releasing composition further comprises a cyclo-oligomer component. In a preferred embodiment, the cyclo-oligomer component is at least effective in sequestering interfering components. Interfering components, without limitation, include hydrophobic molecules, such as lipids. Interfering components interfere with the measurement of the vitamin D component, and therefore, its sequestration substantially reduces interference of the measurement. For example, lipids have been shown to erroneously increase the measurement values of a vitamin D component.

In a preferred embodiment, the cyclo-oligomer component comprises an α-cyclodextrin. In a more preferred embodiment, the cyclo-oligomer component comprises a β-randomly methylated cyclodextrin. The cyclo-oligomer component may also include, without limitation, derivatives of α-cyclodextrin, β-cyclodextrin, derivatives of β-cyclodextrin, γ-cyclodextrin, derivatives of γ-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. As used herein, the term "derivatives" as it relates to a cyclodextrin means any substituted or otherwise modified compound, which has the characteristic chemical structure of the parent cyclodextrin.

In one embodiment, the releasing composition comprises about 0.01 to about 5% of the cyclo-oligomer component. For example, in a preferred embodiment, the releasing composition comprises about 2% of an α-cyclodextrin. In another preferred embodiment, the releasing composition comprises about 0.05% of a β-randomly methylated cyclodextrin. In an alternative embodiment, the releasing composition is substantially free of a cyclo-oligomer component.

In one embodiment, the releasing component further comprises a salicylate and the like, such as 8-anilino-1-naphthalenesulfonic acid (ANS). Without wishing to be limited by any theory or mechanism of operation, it is believed that the salicylate or the like of the present invention is at least effective to release the vitamin D component from binding to proteins and/or solubilize the vitamin D component in the releasing composition. In a preferred embodiment, the salicylate is a metal salicylate, for example sodium salicylate. The release composition preferably comprises about 0.5 to about 5% of a metal salicylate, for example a sodium salicylate. In an alternative embodiment, the releasing composition is substantially free of a salicylate and the like.

In one embodiment, the releasing component further comprises a surfactant and the like. Without wishing to be limited by any theory or mechanism of operation, it is believed that the surfactant and the like of the present invention is at least effective to block the vitamin D component from being attached to lipids, proteins and the like. In a preferred embodiment, the surfactant is TWEEN-20 or TRITON X-100. The releasing composition of the present invention may include about 0.01 to about 0.1% of a surfactant. For example, 0.05% of TWEEN-20 may preferably be employed in the present invention. In another preferred embodiment, the releasing component is substantially free of a surfactant.

The releasing composition of the present invention may comprise an aqueous base component and may be substantially free of the cyclo-oligomer component, the salicylate and the surfactant. In a preferred embodiment, the release component comprises an aqueous base component and at least a cyclo-oligomer component, a salicylate and/or a surfactant. In a more preferred embodiment, the release component comprises an aqueous base component and a cyclo-oligomer component. In an even more preferred embodiment, the release component comprises an aqueous base component, a cyclo-oligomer component and a salicylate. For example, a preferred releasing composition comprises about 0.1 to about 1 M of an aqueous base component, about 0.01 to about 5% of a cyclo-oligomer component and about 0.01 to about 5% of a salicylate.

As discussed above, the releasing composition of this invention is adaptable for use in or with various bio-assay techniques known in the art to determine the concentration of a vitamin D component. For example, in one embodiment, a kit of the present invention comprises a releasing composition and a detecting composition.

In a broad embodiment, the detecting composition of the present invention comprises a host component. Preferably, the detecting composition further comprises a partner component. The host component is any molecule or set of molecules capable of selectively binding to a partner component or a vitamin D component. For example, a host component may be an aptamer or a molecular imprint polymer. In one embodiment, a host component is an antibody, or a portion of an antibody, for example a Fab portion, capable of binding to a partner component. The antibody of the present invention may be monoclonal or polyclonal.

Various methods are known in the art to produce an antibody specific toward a certain antigen, for example a partner component. For example, an antibody may be raised from a rabbit injected with an antigen, the antigen being the partner component or a part thereof. Additionally, synthetic antibodies may also be made. (See U.S. Pat. No. 5,110,833, the disclosure of which is incorporated in its entirety by reference herein.)

The specific composition of the partner component depends on the nature of the assay. For example, if a competitive assay technique is employed, the partner component may comprise a competing molecule which is capable of competing with the released vitamin D component at the binding site of the host component to form a partner/host complex. Preferably this competing molecule is linked to a separator component, wherein the separator component eventually facilitates in separating out and isolating the partner/host complex. The separator component may, without limitation, comprise a peptide, an antibody, a small molecule, a polymer particle and/or a magnetic particle. The competing molecule may be linked to the separating component by various means known in the art. For example, the molecule may be linked to the separator component through a chemical bond or via an antibody.

In one embodiment, the separator component may be isolated from solution, along with anything else which is presently attached to it, for example a competing molecule, by various means. For example, if the separating component is an antibody, an Enzyme-Linked-ImmunoSorbent Assay (ELISA) technique or the like may be employed to isolate the separating component. If the separating component is a magnetic particle, then a magnetic field may be employed to isolate the separating component from solution.

In one embodiment, the partner component comprises a vitamin D component linked to a solid phase, for example a particle, preferably a magnetic particle. In a preferred embodiment, the vitamin D component directly links to a particle. For example, a 3-hydroxyl of the 25-OH-D (a vitamin D component) may form a direct covalent bond with a functional group present on a particle; such group includes, without limitation, —COOH, —NH2, epoxide, tosyl, and —SH. In a more preferred embodiment, the vitamin D component links to a particle through at least one linking component, for example a biotin, derivatives thereof and the like. (see Holick et al U.S. Pat. No. 5,981,779, the disclosure of which is incorporated in its entirety herein by reference). For example, in one embodiment, the partner component comprises a 25-OH-D linked to a magnetic particle via a biotin.

In one embodiment, a partner component competes with the vitamin D component, for example, the released 25-OH-D, to bind to the host component, for example an antibody, to form a partner/host complex. The partner/host is then isolated and its concentration is determined. The concentration of the vitamin D component, for example the 25-OH-D, should be directly proportional to the concentration of the partner/host complex.

In an alternative embodiment, the partner component comprising a competing molecule linked to a separator component competes with the vitamin D component to bind to one or more intermediate binding components. At least one of the intermediate binding components has a binding site for a vitamin D component. In this case, the host component can form a complex with the partner component through an intermediate binding component. (When the partner component forms an a complex with a host component through an intermediate component, a partner/intermediate/host complex is formed. The partner/intermediate/host complex may sometimes be referred to herein as the "partner/host" complex for clarity.) For example, in one embodiment, the partner component comprises a 25-OH-D linked to a magnetic particle through a biotin, and this partner component competes with a released 25-OH-D at the binding site of an intermediate binding component, for example a DBP. After the partner component binds to the intermediate binding component, the host component, for example an antibody, may form a complex with the partner component through the intermediate binding component, by binding to the intermediate component. In a preferred embodiment, the host component antibody which binds to a DBP (hereinafter "anti-DBP") is a rabbit antibody purchased under the trade name Rabbit Anti-Human Gc-Globulin from DAKO in Denmark.

Furthermore, the host component may be present when the partner component competes with the vitamin D component to bind to the intermediate binding component; or the partner/intermediate complex may be first isolated from solution and the host component is subsequently introduced to form a partner/intermediate/host complex.

The concentration of the partner/host complex formed in accordance with this invention should be proportional to the concentration of the vitamin D component being measured. (Herein after and throughout "partner/host complex" may refer to a partner/host complex or partner/intermediate/host complex.) In one embodiment, the concentration of the partner/host complex may be measured by isolating the partner/host complex and measuring the level of the host component and/or measuring the level of the intermediate component if the partner component forms a complex with the host component through an intermediate component. Various methods known in the art may be adapted and employed to measure the concentration of the host component and/or the intermediate component.

For example, in one embodiment, the host component and/or the intermediate component (hereinafter "signal compounds") may be labeled. Preferably, the signal compound is labeled at a position where the signal compound may still bind to a partner component and the label may still be detected. Labels which may be employed in accordance with this invention include, without limitation, chemiluminescent molecules, fluorescent molecules, enzymes, co-enzymes, isotopes and sensitizers.

Chemiluminescent molecules useful in this invention include, without limitation, luciferin, luminol, pyrogallol, isoluminol, aequorin, cyclic arylhydrazides, dioxetanes, rhodium chelates (electrochemiluminescent), oxalate esters, thermochemiluminescent labels, acridinium and the like. These labels may be attached to a protein, for example an anti-DBP, with techniques well known in the art. (See U.S. Pat. No. 5,284,952, the disclosure of which is incorporated in its entirety herein by reference.) In one embodiment, a signal compound such as an anti-DBP may be labeled with an acridinium by employing the methods found in U.S. Pat. No. 5,284,952. (See also U.S. Pat. Nos. 5,110,932 and 5,338,847, the disclosures of which are incorporated in their entirety herein by reference.) In this embodiment, the acridinium labels the lysine residue of the anti-DBP. It has been shown that a sufficient number of the anti-DBP is labeled at the appropriate places to be effective as a labeled host component.

Fluorescent molecules useful in this invention include, without limitation, umbelliferone, fluorescein, rhodamine, Texas red dyes, pthalocyanines, coumarin, squaraine, anthracene, erythrosine, europium chelates and the like. For example, a signal compound such as a DBP may be labeled with an umbelliferone. (See also, U.S. Pat. No. 3,901,654, the disclosure of which is incorporated in its entirety by reference herein.)

Enzymes useful in this invention include enzymes capable of catalyzing a reactant to produce a product, wherein the product can be detected. Exemplary enzymes which have been developed and used in an assay are those described in U.S. Pat. Nos. 3,654,090; 3,791,932; 3,839,153; 3,850,752; U.S. Pat. Nos. 3,817,837; 3,879,262; Journal of Immunological Methods 1: 247(1972); and the Journal of Immunology 109:129(1972), the disclosures of which are incorporated in their entirety herein by reference. Other enzymes which may be used in accordance with this invention includes glactsidase, gluconidase, phosphatase, peptidase, alkaline phosphatase and the like. In one embodiment, an enzyme in accordance with this invention may be able to catalyze a chemiluminescent reactant, wherein one of the resulting product is a light signal, which can be detected.

Co-enzymes useful in this invention include molecules and/or proteins which facilitate an enzyme to catalyze a reactant to produce a detectable product, for example light. A co-enzyme may include, without limitation, FAD and NAD. In one embodiment, an anti-DBP may be labeled with a NAD. (See for example, U.S. Pat. No. 4,380,580, the disclosure of which is incorporated in its entirety herein by reference.)

Isotopes useful in this invention include, without limitation, $H^3$, $P^{32}$ and $F^{18}$. Other labels may include a non-active precursor of a spectrophotometrically-active substance (British Pat. No. 1,392,403 and French Pat. No. 2,201,299, which patents correspond to U.S. Pat. No. 3,880,934) and electron spin resonance moieties (U.S. Pat. No. 3,850,578).

Sensitizers useful in this invention include, without limitation, those disclosed in U.S. Pat. No. 5,705,622, the disclosure of which is incorporated in its entirety herein by reference. For example, an acceptor molecule may be attached to a DBP and an acceptor molecule may be attached to a vitamin D component.

Various kits comprising a releasing composition and a detecting composition as disclosed in this invention may be used for determining the concentration of a vitamin D component. However, such are only examples of the many possible kits which may employ a releasing composition to assay for a vitamin D component. Other kits are contemplated to be within the scope of this invention. For example, the following patents, articles and instruction manuals disclose assay methods which may be adapted to include a releasing composition of the present invention: U.S. Pat. No. 4,935,339 (discloses a delayed capture assay); U.S. Pat. No. 4,121,1978; U.S. Pat. No. 5,232,836; U.S. Pat. No. 5,064,770; U.S. Pat. No. 5,202,266; U.S. Pat. No. 4,816,417; U.S. Pat. No. 5,821,020 and U.S. Pat. No. 5,981,779; Competitive Protein-Binding Radioassays for 25-OH-D by Haddad; Instruction Manual of Jummun Diagnostik Entitled 25-OH Vitamin D Enzyme-based Protein-Binding-Assay; Instruction Manual of Incstar Catalog No. 68100; Directional insert of Nichols Institute entitled 25-OH-D 60T Kit; Directional Insert of BioSource Europe S.A. entitled 25OH-VIT.D3-RIA-CT; Directional Insert of IDS, Inc. entitled Gamma-B25-Hydroxy Vitamin D RIA AA-35PS (Jan. 6, 1999, issue 3); Journal of Pharmaceutical and Biomedical Analysis 20 (1999); Determination of Vitamin D3 metabolites/state-of-the-art by Luque de Castro, et al.; Clin. Chem. 30/11, 1731–1736 (1984); Two Direct (Nonchromatographic) Assays for 25-hydroxyvitamin D by Bouillon, et al. The disclosures of which are incorporated in their entirety by reference herein. One adaptation would be to replace the compositions used therein with the present releasing composition.

Without limitation, Table I identifies some general assays (A through H) in which a releasing composition of this invention may be employed. Assay A has been discussed above.

Assay B may similarly employ a releasing composition to release the vitamin D component of a body fluid sample. Once released, it may be added to a composition or a series of compositions comprising a labeled DBP and a vitamin D component linked to a separator component, for example a magnetic particle. Preferably, the released vitamin D component does not have to be purified prior to adding to said composition. In other words, a composition comprising a labeled DBP and a vitamin D component linked to a separator component may be added to the homogeneous mixture of body fluid sample and releasing composition.

Assays C through G may similarly employ a releasing composition to release the vitamin D component from a body fluid sample. Once released, a detecting composition or series of detecting compositions, comprising the components identified in the respective assays, may be added. In assay G, the conditions conducive for the binding of the biotin to the avidin may be similar to that disclosed in U.S. Pat. No. 5,395,938, (Title: Biotinylated Chemiluminescent Labels and Their Conjugates, Assays and Assay Kits), the disclosure of which is incorporated in its entirety herein by reference.

Assay H may also employ a releasing composition of the present invention to release the vitamin D component from a body fluid sample. After it is released the vitamin D component is allowed to bind directly to a host component, for example an antibody. The released vitamin D component is also allowed to bind to a labeled antibody. Preferably the host component and the labeled antibody are able to bind to different determinants of the released vitamin D component. (See U.S. Pat. No. 5,641,690, which discloses immunometric assay methods, the disclosures of which are incorporated in its entirety herein by reference). The host/vitamin-D/labeled antibody complex may be isolated and counted utilizing techniques commonly known in the art, for example ELISA.

In a broad embodiment, the kit of the present invention may be adapted to be employed in an automated assay system to determine the concentration of a vitamin D component. For example, the kit of the present invention may preferably be used in conjunction with the Nichols Advantage system.

EXAMPLE 1

An Automated Method for Detecting a 25-OH-D

Currently, immunoassays measuring the concentration of 25-OH-D use organic solvents to release the 25-OH-D. The addition of an organic solvent to the serum results in either a precipitate or a two-layer liquid. Thereafter, the layer containing the released 25-OH-D is (manually) separated and is mixed with another composition to measure the concentration of the 25-OH-D. The step of separating the 25-OH-D is (a) time consuming, and (b) a source of error in the assays, especially if the separation step is performed manually.

The present invention eliminates the need to purify or substantially purify the released 25-OH-D prior to determining its concentration and allows for automation of the assay. In this example, the automated release of the 25-OH-D from a binding protein and determination of the 25-OH-D concentration are performed on the Nichols Advantage system. This process is wholly automated. Manual pipetting and centrifugation are not needed. The assay kit use in conjunction with the Nichols Advantage System includes a release composition and detecting composition.

Releasing Composition

The releasing composition comprises an aqueous base component (0.1–1.0 M NaOH), beta-randomly methylated cyclodextrin (0.01–5%), and sodium salicylate (0.01–5%). The pH of the releasing composition is about 13.

Detecting Composition

The detecting composition comprises a magnetic particle suspension with 25-OH-D immobilized on the surface, a DBP, an anti-DBP and stabilizers. Also, the detecting composition has a pH of about 6 to about 9, preferably 8.3. Furthermore, the detecting composition also has a buffer capacity to bring the pH of the total mixture (the homogeneous mixture and the detecting composition) into the range where the DBP is stable and capable of binding 25-OH-D. Preferably the total mixture has a pH of about 6 to about 9, preferably 8.3. The buffer system used comprises 200 mM TRIS, 150 mM NaCl, 0.9% gelatin, 1% bovine serum albumin and 0.09% sodium azide.

The streptavidin coated particles are about 0.5–5 microns in size, and may be purchased from Seradyne, Dynal, Bangs Laboratories. The 25-OH-D is attached to the particle via a biotin or the like (Holick et al U.S. Pat. No. 5,981,779, the disclosure of which is incorporated in its entirety herein by reference). The amount of particles used in the assay is about 5 to about 30 uL (preferably 25 uL) of a 1.25–2.5 mg/mL suspension.

The concentration of the DBP is in the range about 0.2 to about 1.0 ug/mL and is added to the assay in the amount of about 10 to about 280 uL, preferably about 250 uL.

The anti-DBP, preferably purchased from DAKO, is labeled with an acridinium sulfonyl chloride derivative, a chemiluminescent label. Preferably, the acridinium derivative is labeled by a method disclosed in U.S. Pat. No. 5,284,952, the disclosure of which is incorporated in its entirety herein by reference. In brief, the conjugate is prepared by adding the reactive label in acetonitrile to the antibody in carbonate buffer at pH 9.6. The reaction proceeds at ambient temperature for a period of about half an hour and the unattached label is removed by gel filtration chromatography. The labeled anti-DBP is diluted to a concentration of about 0.2–10 ug/mL in buffer with a pH of about 6.0. The amount of acridinium labeled anti-DBP that is added to the assay is about 10 to about 280 uL, preferably about 50 uL.

In preferred embodiments, a stabilizer may be added to a composition of the assay. For example, a stabilizer may be added to the detecting composition. Stabilizers include gelatin, bovine serum albumin, egg albumin, polyethylene glycol, poly vinyl alcohol, poly vinyl pyrrolidone and the like and mixtures thereof. These stabilizers may be effective in blocking of the non-specific binding of the assay components.

About 10–100 uL, preferably 20 uL, of a patient body fluid sample and about 10–100 uL, preferably 60 uL, of the releasing composition are pipetted into a holder, for example a cuvette well, forming a homogeneous mixture. The releasing composition acts on the patient sample in an incubator at a constant temperature (about 25–37° C., preferably 37° C.) for a specified time (1–60 min., preferably 21 min.). When the release is complete, a detecting component is pipetted directly into the homogeneous mixture, forming a total mixture. The total mixture is incubated for about 30 min to about 60 min., preferably about 42 min. During this incubation period the 25-OH-D-biotin-magnetic-particle competes with the 25-OH-D of the patient's sample to form a complex with the labeled-DBP. Subsequently, the 25-OH-D-biotin-magnetic-particle/labeled-DBP complex is isolated by a wash. The concentration of the complex is determined by a chemiluminescent reading. The concentration of the complex is inversely proportional to the concentration of the 25-OH-D concentration in the patient's sample.

In addition to decreasing the labor requirements, this assay method allows for positive patient identification. Positive patient identification can be achieved because the Nichols Advantage system pipettes the detecting composition directly into the sample holder containing the releasing composition and the body fluid, and every sample holder has a bar code to which the result matches.

EXAMPLE 2

Precision of Assays: Intra CV

Intra Coefficient of Variation (CV) studies for the determination of the 25-OH-D were conducted with various systems, including a system using a kit of the present invention in conjunction with Nichols automated assay machine, the Nichols Advantage. The studies using the kit of the present invention and Nichols Advantage automated technique involves obtaining a patient sample and performing the assay 20 times. The results are shown in Table I.

TABLE I

|  | Dose (ng/ml) | CVD |
|---|---|---|
| Nichols | 12.3 | 7.7% |
| Advantage | 34.6 | 3.5% |

TABLE I-continued

|  | | |
|---|---|---|
| Automated assay Run #1 | 86.0 | 2.0% |
| Nichols | 9.5 | 14.1% |
| Advantage | 46.8 | 2.6% |
| Automated assay Run #2 | 58.6 | 2.6% |

|  | Dose | CVD |
|---|---|---|
| $^{125}$I Assay Kit #1 | | |
|  | 26.5 | 5.3% |
|  | 58.4 | 5.0% |
|  | 151.0 | 6.1% |
| $^{125}$I Assay Kit #2 | | |
|  | 8.6 | 11.7% |
|  | 22.7 | 10.5% |
|  | 33.0 | 8.6% |
|  | 49.0 | 12.5% |

Each patient sample was assayed 20 times. Of the 20 results, a mean and a standard of deviation were determined. CV=(standard of deviation/mean)×100. CVD is CV of Dose, wherein Dose is the concentration of the 25-OH-D. The lower the CV, the better the precision of measurement. For example, a good CVD is <8%.

For each Dose range, the CVDs of the assays using an assay kit of the present invention in conjunction with the Nichols Advantage system are better than other assay systems. For example, the assay kit of the present invention has a CVD of 2.6% at a Dose of 46.8; the $^{125}$I Assay Kit #2 has a CVD of 12.5% at a Dose of 49.0; and the $^{125}$I Assay Kit #1 has a CVD of 5.0% at a Dose of 58.4.

EXAMPLE 3

Luminol Chemiluminescent Direct Labeling of DBP

About 1 mg of Vitamin D binding protein, DBP, is buffer exchanged three times with 100 mM PBS at pH 8.2. The final volume was 200 uL. Succinyl-amino-buty-ethyl-isoluminol NHS ester (4.6 mg) is dissolved in DMF. The isoluminol (17 uL) is added to the DBP and the mixture is maintained at room temperature for about 1 hour with occasional shaking. The unreacted label is removed by size exclusion chromatography using SEPHADEX-G25 (23×1 cm) and 100 mM PBS, pH 6.0 as the mobile phase.

EXAMPLE 4

Direct Chemiluminescent Direct Labeling of DBP

About 1 mg of Vitamin D binding protein, DBP, is buffer exchanged three times with 20 mM sodium carbonate buffer at pH 9.6. The final volume is 500 uL. Two aliquots of fluorescein-5-isothiocyanate (FITC) are dissolved in DMF just prior to addition to give a concentration of 1.25 mg/mL. The first FITC aliquot (5 uL) is added and the mixture is allowed to react at room temperature. After 15 minutes the second aliquot (5 uL) is added and the reaction proceeds for an additional 15 minutes. The unreacted label is removed by size exclusion chromatography using Sephadex G-25 (2 cm×33 cm) and 100 mM, pH 7.4 mobile phase.

EXAMPLE 5

Biotin Direct Labeling of DBP for "Upside-Down" Assay

About 2.0 mg of DBP is buffer exchanged with 20 mM bicarbonate at pH 9.6 three times to give a final volume of 1.0 mL. Two aliquots of sulfo-NHS-LC-biotin (Pierce) are dissolved in water to give a 1 mg/mL solution just prior to addition. The first aliquot (10 uL) is added and the reaction is maintained at room temperature for 5 minutes. The second aliquot (10 uL) is added and the reaction proceeds for an additional 4 minutes. The unreacted biotin is removed by size exclusion chromatography using SEPHADEX G-25 and 100 mM PBS, pH 7.4 as the mobile phase.

EXAMPLE 6

Acridinium Direct Labeling of anti-25-Hydoxyvitamin D Monoclonal Antibody 2.5 mg of antibody is buffer exchanged into 20 mM bicarbonate buffer, pH 9.6, three times to give a final volume of 1.75 mL. Sulfonylchloride acridinium ester is dissolved in sufficient acetonitrile to give a 1.75 mg/mL solution. The acridinium ester (52.5 uL) is added to the antibody and the reaction mixture is maintained at room temperature about 0.5 hour. The unreacted label is removed by size exclusion chromatography using SEPHADEX G-75 and 100 mM PBS, pH 6.0 as the mobile phase.

EXAMPLE 7

Acrdinium Indirect Labeling

Anti-DBP (Dako) is buffer exchanged to yield 2.2 mg of protein in 1.1 mL of pH 9.6, 20 mM bicarbonate buffer. A solution of sulfonylchloride acridinium ester (1.6 mg/mL) is in acetonitrile. The acridinium (4.4 uL) is added to the antibody and the reaction mixture is maintained at room temperature for 15 minutes. A second aliquot of acridinium (4.4) uL is added for and additional 15 minutes. The unreacted label is removed by chromatography on a mixed bed column (SEPHAROSE 6B/SEPHADEX G-75, 1.5 cm×48 cm).

EXAMPLE 8

Direct Labeling of DBP with HRP

Activated peroxidase from Boehringer Mannheim Biochimica is used for labeling. The DBP (4 mg) is dissolved in pH 9.8, 100 mM carbonate buffer (1 mL). This solution is added to the POD (8 mg). The reaction proceeded at room temperature for 1 hour. The conjugation is quenched by addition of 120 uL of triethanolamine solution (pH 8, 30%). Sodium borohydride (150 uL) freshly dissolved in water (8 mg/mL) is added to the solution maintained at room temperature for about 0.5 hour. Additional sodium borohydride (75 uL) is provided and the reaction proceed for an additional 2 hours at room temperature. The conjugate is dialyzed with pH 6.0 PBS with glycine.

While this invention has been described with respect to various specific examples and embodiments, it is to be understood that the invention is not limited thereto and that it can be variously practiced with the scope of the following claims.

What is claimed is:

1. A kit for determining a concentration of 25-hydroxy vitamin D (25-OH-D) in a sample, comprising:
   a releasing composition including from about 0.01 to about 5% of a cyclodextrin, from about 0.01 to about 5% of a sodium salicylate, and from about 0.1 to about 1.0 M NaOH, the cyclodextrin, the salicylate, and the NaOH being provided in an amount effective to reduce interference from a protein or a lipid with 25-hydroxy vitamin D present in a sample;
   25-hydroxy vitamin D coupled to a solid phase;
   vitamin D binding protein; and
   a vitamin D binding protein antibody coupled to a label present in an amount that produces a detectable signal when 25-hydroxy vitamin D is present in the sample.

2. A kit of claim 1, wherein the cyclodextrin, the salicylate, and the NaOH are provided in an amount effective to reduce interference from proteins or lipids with 25-hydroxy vitamin D present in a sample of a mammal fluid.

3. A kit of claim 2 wherein the mammal fluid is selected from the group consisting of milk whole blood, serum, and plasma.

4. A kit of claim 2 wherein the mammal fluid comprises a human serum.

5. A kit of claim 1 wherein the releasing composition comprises about 0.35 to about 0.5 M of NaOH.

6. A kit of claim 1 wherein the releasing composition is free of an organic solvent.

7. A kit of claim 1 wherein the cyclodextrin is selected from the group consisting of alpha-cyclodextrin and a beta-methylated cyclodextrin.

8. A kit of claim 1 wherein the releasing composition comprises about 2% of an alpha-cyclodextrin.

9. A kit of claim 1 wherein the releasing composition comprises about 0.05% of a beta-methylated cyclodextrin.

10. A kit of claim 1 wherein the releasing composition comprises about 0.5 to about 5% of the sodium salicylate.

11. A kit of claim 1 wherein the releasing composition further comprises about 0.01 to about 0.1% of a surfactant.

12. A kit of claim 1 wherein the releasing composition forms a homogeneous mixture with a mammal fluid.

13. A kit of claim 1 wherein the label is selected from the group consisting of a chemiluminescent label, a fluorescent label and a radio-active label.

14. A kit of claim 1 wherein the vitamin D binding protein antibody is an acridinium-labeled antibody.

15. A kit of claim 1 wherein the solid phase is a magnetic particle.

16. A kit of claim 1 wherein the 25-hydroxy vitamin D coupled to a solid phase is in the form of 25-hydroxy vitamin D coated magnetic particles, the vitamin D binding protein antibody is coupled to an acridinium label, and the 25-hydroxy vitamin D coated magnetic particles, the acridinium labeled vitamin D binding protein antibody, and the vitamin D binding protein are present in a single composition.

17. A kit of claim 1, wherein the releasing composition further includes from about 0.01% to about 0.1% of a surfactant, and the antibody is labeled with acridinium.

* * * * *